United States Patent [19]

Moss

[11] 4,263,917

[45] Apr. 28, 1981

[54] METHOD OF SEALING BILE DUCT DURING CHOLANGIOGRAPHY

[76] Inventor: James P. Moss, 250 E. Liberty St., Louisville, Ky. 40202

[21] Appl. No.: 27,739

[22] Filed: Apr. 6, 1979

[51] Int. Cl.³ .............................................. A61B 5/00
[52] U.S. Cl. .................................. 128/656; 128/344; 128/349 B
[58] Field of Search ................... 128/325, 344, 349 B, 128/658, 656, 246, 348

[56] References Cited

U.S. PATENT DOCUMENTS

| | | | |
|---|---|---|---|
| 1,598,284 | 8/1926 | Kinney | 128/349 B X |
| 1,643,289 | 9/1927 | Peglay | 128/246 |
| 2,691,985 | 10/1954 | Newsom | 128/325 |
| 3,050,066 | 8/1962 | Koehn | 128/325 X |
| 3,053,257 | 9/1962 | Birtwell | 128/349 B |
| 3,448,739 | 6/1969 | Stark et al. | 128/658 |
| 4,085,757 | 4/1978 | Pevsner | 128/348 |

*Primary Examiner*—Dalton L. Truluck
*Attorney, Agent, or Firm*—Larson, Taylor and Hinds

[57] ABSTRACT

A self-sealing catheter apparatus and method are disclosed which are broadly useful in medical surgery and particularly to perform cholangiography or in connection with perfusion of the coronary arteries during open heart surgery. The catheter provides means for sealing a duct and introducing dye into the duct once the catheter has been placed inside of the duct. An inflatable balloon sleeve and adjacent reservoir are mounted near the distal end of the catheter. The distal end of the catheter is inserted into the duct until the reservoir contacts the outer wall of the duct and the balloon sleeve is thus located inside of the duct. Then, the reservoir is depressed forcing the fluid contained therein to inflate the balloon sleeve. The inflated balloon sleeve not only seals the duct against the passage of fluids therethrough, but also holds the catheter in place inside of the duct. The dye is then introduced into the duct via the catheter lumen.

2 Claims, 5 Drawing Figures

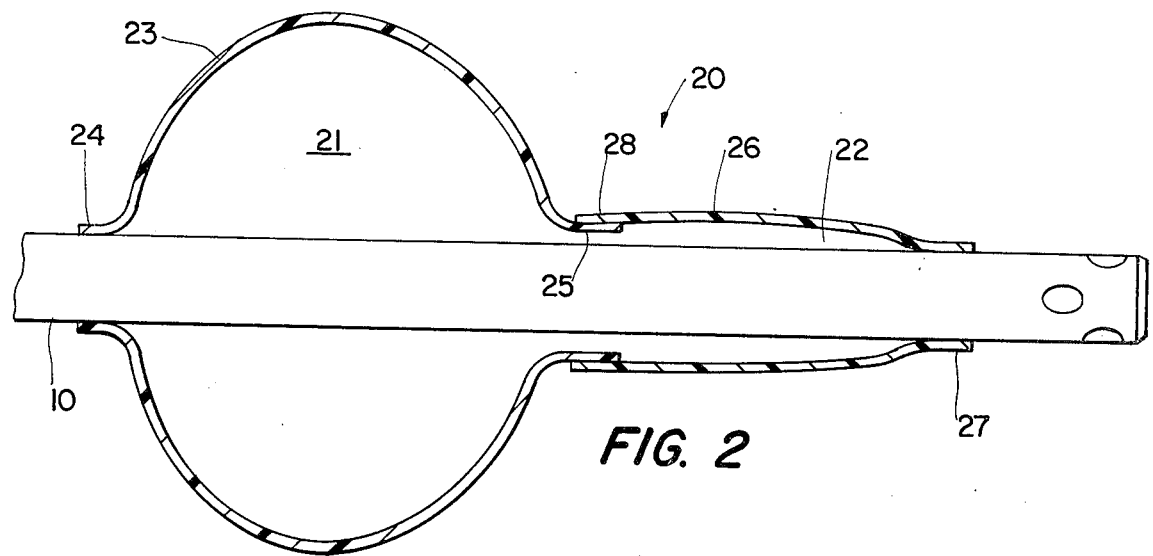
FIG. 2
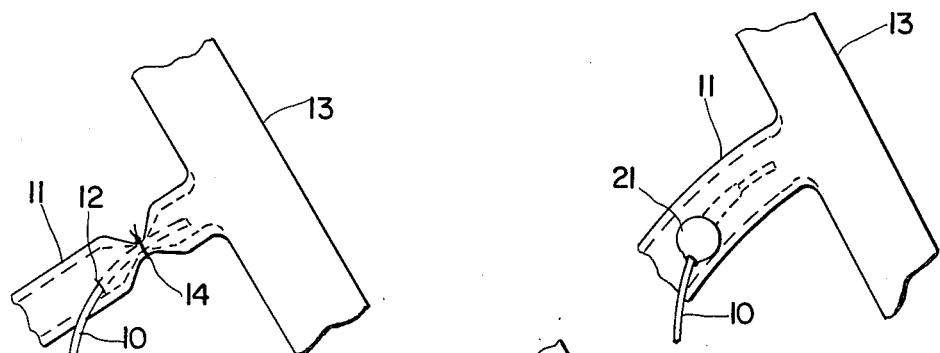
PRIOR ART
FIG. 1
FIG. 4
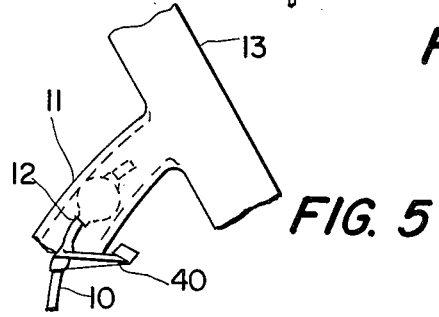
FIG. 5
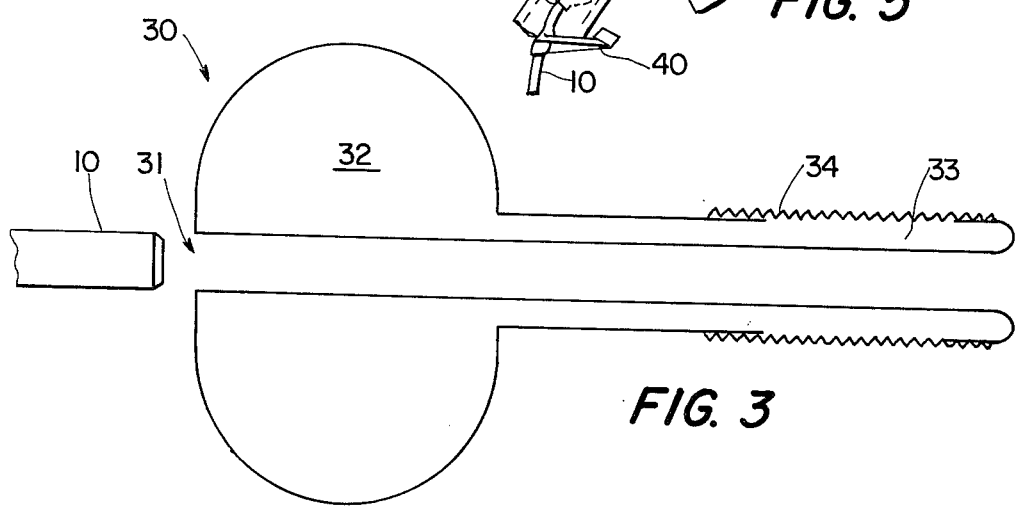
FIG. 3

METHOD OF SEALING BILE DUCT DURING CHOLANGIOGRAPHY

FIELD OF THE INVENTION

This invention relates generally to catheters and more particularly to a self-sealing catheter having a balloon thereon.

BACKGROUND OF THE INVENTION

It has become increasing useful during cholecystectomies (surgical excision of the gallbladder) to perform operative cholangiography to prevent retained biliary calculi (stones). Operative cholangiography consists of X-rays taken during the operative procedure by the introduction of radio-opaque dye into the extrahepatic biliary tree. When roentgenograms are made following the introduction of this dye, stones and related problems within these ducts are often apparent at the time of the initial operative procedure and may be easily dealt with at that time.

One means of introducing the dye into the common bile duct is by insertion of a thin-walled needle directly through the wall of the common bile duct into its lumen. While this may be performed quickly, a number of problems may result from this method. The small needle hole is often a source of bile leakage into the operative site. In addition, the needle tends to become dislodged during dye insertion necessitating repeated insertions and the formation of multiple puncture wounds in the common duct.

A second means of introducing dye into the common bile duct, as shown in FIG. 1, is to make a small incision in the cystic duct. Through this small incision, a catheter is threaded into the cystic duct until the distal end of the catheter is near the common duct. Then the proximal end of the catheter is connected to a source of dye, and this dye is injected through the catheter to outline the interior of the bile ducts. This is the procedure which is most commonly used. However, some disadvantages of this procedure are that the operative field is often difficult to expose and the catheter must be manipulated with long forceps or clamps. In addition, a suture or surgical ligature must be placed around the cystic duct to secure the catheter in place and to prevent backflow of the dye. Unfortunately, the catheter still tends to become dislodged and reinsertion is difficult. Another drawback to the use of a conventional catheter is that the surgeon may thread the catheter into the duct for an extensive distance and the catheter may pass through the cystic duct and into the common bile duct and perforate the wall of the common duct.

Thus, the prior art has failed to provide a safe and easily usable means for introducing dye into the bile ducts. In particular, the use of a needle is unsafe while the use of a catheter is cumbersome and difficult.

SUMMARY OF THE INVENTION

The present invention provides a novel apparatus and a novel method for introducing dye into bile ducts. The present invention also provides a means for retaining the catheter in the duct and for preventing the backflow of dye in the duct.

It is a feature of the present invention that a catheter is provided with a balloon on the distal end of the catheter. So-called Foley balloon catheters with retention balloons near the ends have been disclosed in the prior art for draining the bladder in such U.S. Pat. as: Nos. 3,044,468 and 3,547,126 to Birtwell; 3,152,592 to Foley; 3,599,620 to Balin; 3,602,226 to Ericson; and 3,924,634 to Taylor et al. However, the Foley balloon catheter is intended to be used to drain the bladder or the like. The balloon portion must be inflated only inside of the bladder where it serves to hold the catheter inside the bladder. Accidental inflation of the balloon of the Foley balloon catheter while it is still in a duct often results in rupturing the duct and subsequent serious complications. Therefore, it is a further feature of the present invention to provide for a small reservoir for the balloon on a catheter so that the balloon will not rupture a duct when it is inflated inside of the duct.

It is also a feature of the present invention to provide a self-sealing catheter which is inserted in a duct until the reservoir contacts the outer wall of the duct. With the reservoir so positioned, the balloon is properly positioned inside the duct and the balloon is then inflated to block the duct.

It is an object of the present invention to provide a simple and reliable self-sealing catheter for introducing dye into the bile ducts. It is also an object of this invention to provide a self-sealing catheter which is safe to operate due to the fact that the reservoir used to inflate the balloon contains only sufficient fluid to inflate the balloon to the proper size so that the balloon cannot rupture the duct.

Other features, objects and advantages of the present invention are stated in or apparent from the presently preferred embodiments of the invention found hereinbelow.

BRIEF DESCRIPTION OF THE DRAWINGS

FIG. 1 is a schematic representation of a prior art means for introducing dye into the bile ducts via a catheter.

FIG. 2 is a partial cross-sectional side view of one embodiment of the present invention.

FIG. 3 is a partial cross-sectional side view of another embodiment of the present invention.

FIGS. 4 and 5 are schematic representations showing the invention being used to block a duct before introducing dye into the duct.

DETAILED DESCRIPTION OF THE PREFERRED EMBODIMENTS

With reference now to the drawings in which like numerals represent like elements throughout the several views, a prior art method for injecting dye into a bile duct is depicted in FIG. 1. To employ this prior art method, a catheter 10 is used which is formed by an elongate tube having a distal end for insertion in a duct and a proximal end which remains outside of the duct and which has a central lumen extending longitudinally through the tube. Catheter 10 is inserted into cystic duct 11 through a small incision 12 until the distal end of the catheter 10 approaches the intersection of cystic duct 11 and common duct 13. A ligature 14 is then tied around cystic duct 11 and catheter 10 to hold catheter 10 in place and to prevent the backflow of dye in cystic duct 11. The dye is then injected into common duct 13 via catheter 10. As was discussed previously, this widely used method has a number of drawbacks including being difficult to employ and dislodging of catheter 10.

A presently preferred embodiment of the present invention is depicted in FIG. 2. Integrally formed with catheter 10 near its distal end is a fluid-tight enclosure 20. Fluid-tight enclosure 20 includes a reservoir 21 and inflatable balloon 22. Reservoir 21 is bounded by the exterior wall of catheter 10 and reservoir sleeve 23. Contained in reservoir 21 is a suitable fluid, such as air. The diameter of the reservoir may be varied in size to achieve inflation of the balloon 26 to secure proper fit in varying sized anatomical cystic ducts, one appropriate sized diameter being 4 mm. Reservoir sleeve 23 is preferably made of flexible plastic and proximal end 24 of reservoir sleeve 23 is bonded around the periphery of the exterior wall of catheter 10 to form a fluid-tight seal. Inflatable balloon 22 is bounded by the exterior wall of catheter 10 and balloon sleeve 26. Balloon sleeve 26 is made from a resilient material such as latex, causing it to pull itself next to the outer walls of catheter 10 when balloon 22 is not inflated. Distal end 27 of balloon sleeve 26 is bonded around the periphery of the exterior wall of catheter 10 to form a fluid-tight seal. Also bonded together to form a fluid-tight seal are distal end 25 of reservoir sleeve 23 and proximal end 28 of balloon sleeve 26. Fluid-tight enclosure 20 is thus sealed at both ends but fluid communication is provided between reservoir 21 and inflatable balloon 22.

Another preferred embodiment of the present invention similar to the first-mentioned embodiment is depicted in FIG. 3. In this embodiment fluid-tight bulb 30 has a central bore 31 in which catheter 10 is inserted until the distal end of catheter 10 projects beyond the distal end of bulb 30. Central bore 31 can be provided in several different sizes to fit several different sizes of catheters, i.e., 16 ga, 19 ga and 21 ga. Fluid-tight bulb 30 includes a reservoir 32 and an inflatable balloon 33 which are in fluid communication with each other. In order to provide the needed flexibility and resiliency, fluid-tight bulb 30 is made from a suitable plastic material except for a balloon sleeve 34 made from latex. Balloon sleeve 34 is bonded at each end to fluid-tight bulb 30 and forms the expandable wall for balloon 33. Like the firstmentioned embodiment, reservoir 32 contains a suitable fluid, such as air, and has a diameter of approximately 4 mm.

The method of operation for sealing a duct and introducing dye into the duct is depicted in FIGS. 4 and 5 and will be described using the first-mentioned embodiment to perform operative cholangiography. After a small incision 12 has been cut in cystic duct 11, the distal end of catheter 10 is inserted through this incision so that the distal end of catheter 10 heads towards common duct 13. Catheter 10 is inserted into incision 12 until reservoir sleeve 23 contacts the outer surface of cystic duct 11. When reservoir sleeve 23 contacts the outer wall of cystic duct 11, inflatable balloon 12 is then located inside of cystic duct 11. Next, reservoir 21 is depressed causing the air therein to flow into balloon 22 and inflate it. In order to keep reservoir 21 depressed, a spring clip 40 may be attached around reservoir sleeve 23. Alternatively, the reservoir may be made of a semi-rigid plastic so that when compressed with a clamp, it will remain in its crushed position. Inflated balloon 22 acts both to hold catheter 10 in place in cystic duct 11 and to block the flow in cystic duct 11. Next, dye is introduced into the proximal end of catheter 10 and forced to flow through the lumen of catheter 10. The dye flows out of the distal end of catheter 10 and into cystic duct 11 and common duct 13. Balloon 22 acts to prevent any backflow of dye into cystic duct 11 helping to assure that the dye is directed into common duct 13. After the dye has been injected into common duct 13, spring clip 40 is removed from reservoir sleeve 23. Due to the elastic force of balloon sleeve 26, the air in balloon 22 is returned to reservoir 21 as balloon sleeve 26 returns to its uninflated position near the outer walls of catheter 10. With balloon 22 deflated, it is then easy to remove catheter 10 from cystic duct 11. In the embodiment in which the reservoir is made of a semirigid plastic and retains its crushed configuration, the balloon may be deflated by incising the compressed wall of the reservoir.

The method of operation of the second-mentioned embodiment is the same as described above for the first-mentioned embodiment except for the performing of an initial step. This initial step consists of inserting catheter 10 into and through central bore 31 of fluid-tight bulb 30. In the first-mentioned embodiment, this step was not necessary because fluid-tight enclosure 20 was already formed integrally with catheter 10. One advantage of the second-mentioned embodiment is that the length of catheter 10 which extends beyond balloon 22 can be adjusted to suit differing circumstances.

it is believed that the present invention provides an easy to operate and reliable means for introducing dye into a duct. In addition, it is believed that the use of a small reservoir located adjacent the balloon will practically eliminate the rupturing of ducts. While a variety of fluids may be used in the reservoir, a gas is preferred due to the relative compressibility of a gas to a liquid. This compressibility of a gas further reduces the chance of rupturing a duct because the gas in the balloon will compress somewhat as the force on the duct increases.

Other alternative embodiments of the present invention should be apparent to those of ordinary skill in the art. For instance, the reservoir and balloon can be made of other suitable materials besides those mentioned. Also, the fluid in the reservoir could be an inert gas.

Although the invention has been described in detail with respect to exemplary embodiments thereof, it will be understood by those of ordinary skill in the art that variations and modifications may be effected within the scope and spirit of the invention.

I claim:

1. A method for sealing a duct and introducing dye into the duct comprising the steps of:
    inserting a catheter having an inflatable balloon and a depressible reservoir abutting said balloon into the duct until the reservoir contacts the duct;
    inflating said balloon in the duct by said depressible reservoir located in contact with the outside of the duct but adjacent to said balloon so that said balloon fills the duct and blocks the passage of fluid therethrough; and
    introducing the dye into the duct via the catheter lumen;
    such that said catheter is held in place by said balloon and said balloon prevent the backflow of dye in the duct.

2. A method for sealing a duct and introducing dye into the duct as claimed in claim 1 comprising the further step of initially placing an annular fluid-tight bulb on said catheter near its distal end, wherein said bulb includes said depressible reservoir in fluid communication with said balloon.

* * * * *